(12) United States Patent
Chun

(10) Patent No.: US 9,885,081 B2
(45) Date of Patent: *Feb. 6, 2018

(54) DETECTION OF TARGET NUCLEIC ACID SEQUENCES USING DUAL-LABELED IMMOBILIZED PROBES ON SOLID PHASE

(75) Inventor: Jong Yoon Chun, Seoul (KR)

(73) Assignee: Seegene, Inc., Seoul (KR)

( * ) Notice: Subject to any disclaimer, the term of this patent is extended or adjusted under 35 U.S.C. 154(b) by 36 days.

This patent is subject to a terminal disclaimer.

(21) Appl. No.: 13/880,199

(22) PCT Filed: Oct. 20, 2011

(86) PCT No.: PCT/KR2011/007855
§ 371 (c)(1),
(2), (4) Date: Apr. 18, 2013

(87) PCT Pub. No.: WO2012/053850
PCT Pub. Date: Apr. 26, 2012

(65) Prior Publication Data
US 2013/0252827 A1 Sep. 26, 2013

(30) Foreign Application Priority Data
Oct. 22, 2010 (KR) .................. 10-2010-0103599

(51) Int. Cl.
*C12Q 1/68* (2006.01)

(52) U.S. Cl.
CPC ......... *C12Q 1/6874* (2013.01); *C12Q 1/6818* (2013.01); *C12Q 1/6823* (2013.01); *C12Q 1/6837* (2013.01)

(58) Field of Classification Search
None
See application file for complete search history.

(56) References Cited

U.S. PATENT DOCUMENTS

| 5,538,848 | A | 7/1996 | Livak et al. |
| 5,573,907 | A | 11/1996 | Carrino et al. |
| 7,897,736 | B2 | 3/2011 | Reed et al. |
| 7,919,244 | B2 | 4/2011 | Madejón Seiz et al. |
| 8,067,164 | B2 | 11/2011 | Gunning et al. |
| 8,822,673 | B2 * | 9/2014 | Chou et al. ............... 536/26.6 |
| 2005/0042638 | A1 * | 2/2005 | Arnold et al. ............... 435/6 |
| 2007/0059690 | A1 * | 3/2007 | Islam et al. ............... 435/6 |
| 2007/0219367 | A1 * | 9/2007 | Shchepinov ....... G01N 21/6428 536/25.32 |
| 2008/0193934 | A1 * | 8/2008 | Wangh .................. 435/6 |
| 2013/0029331 | A1 * | 1/2013 | Wilson ............. C12Q 1/6823 435/6.11 |

FOREIGN PATENT DOCUMENTS

| WO | WO-92/02638 A1 | 2/1992 |
| WO | WO 2008/011004 A2 | 1/2008 |

OTHER PUBLICATIONS

Liu et al. (TaqMan probe array for quantitative detection of DNA targets, Nucleic Acids Res. 2006; 34(1): e4, Published online Jan. 10, 2006).*
Nazarenko et al. (Effect of primary and secondary structure of oligodeoxyribonucleotides on the fluorescent properties of conjugated dyes, Nucleic Acids Res. May 1, 2002;30(9):2089-195).*
Kouguchi et al. (Real-time nucleic acid sequence-based amplification (NASBA) using an adenine-induced quenching probe and an intercalator dye, J Appl Microbiol. Nov. 2010;109(5):1724-32. Epub Jul. 22, 2010).*
Kricka et al. (Analytical Ancestry: "Firsts" in Fluorescent Labeling of Nucleosides, Nucleotides, and Nucleic Acids, Clin Chem. Apr. 2009;55(4):670-83. 2008.116152. Epub Feb. 20, 2009).*
Pirrung (How to Make a DNA Chip, Angew. Chem. Int. Ed., 41: 1276-1289, Apr. 16, 2002).*
Zuo et al. (Sensitive and Selective Amplified Fluorescence DNA Detection Based on Exonuclease III-Aided Target Recycling, J Am Chem Soc. Feb. 17, 2010;132(6):1816-8. doi: 10.1021/ja909551b).*
Doddridge et al., "Effects of Vinylphosphonate Internucleotide Linkages on the Cleavage Specificity of Exonuclease III and on the Activity of DNA Polymerase I," *Biochemistry* 42(11): 3239-3246 (2003).
Liu et al., "TaqMan Probe Array for Quantitative Detection of DNA Targets," *Nucleic Acids Research* 34(1): e4 (2006).
International Search Report for PCT/KR2011/007855, dated Jun. 20, 2012 (2 pages).
Frayling et al., "PCR-Based Methods for Mutation Detection," Molecular Diagnostics: For the Clinical Laboratorian, Second Edition. Edited by: W.B. Coleman and G.J. Tsongalis. pp. 65-66 (2006).

* cited by examiner

*Primary Examiner* — Aaron Priest
(74) *Attorney, Agent, or Firm* — Clark & Elbing LLP; Susan M. Michaud

(57) ABSTRACT

The present invention relates to a novel method for detection of target nucleic acid sequences on a solid phase using dual-labeled immobilized probes and its resistance to a 5' to 3' exonuclease activity of a DNA polymerase. Because the label is remained on the solid substrate by resistance to nucleases due to labeling of a base component the internal nucleotide, the present invention requires no consideration of a suitability of position of the label for remaining on the solid substrate. The present invention ensures to minimize background signal by positioning labels at a site on probes suitable to maximize quenching efficiency of the dual label system, since it permits to freely determine the position of the internal label on probes.

18 Claims, 6 Drawing Sheets

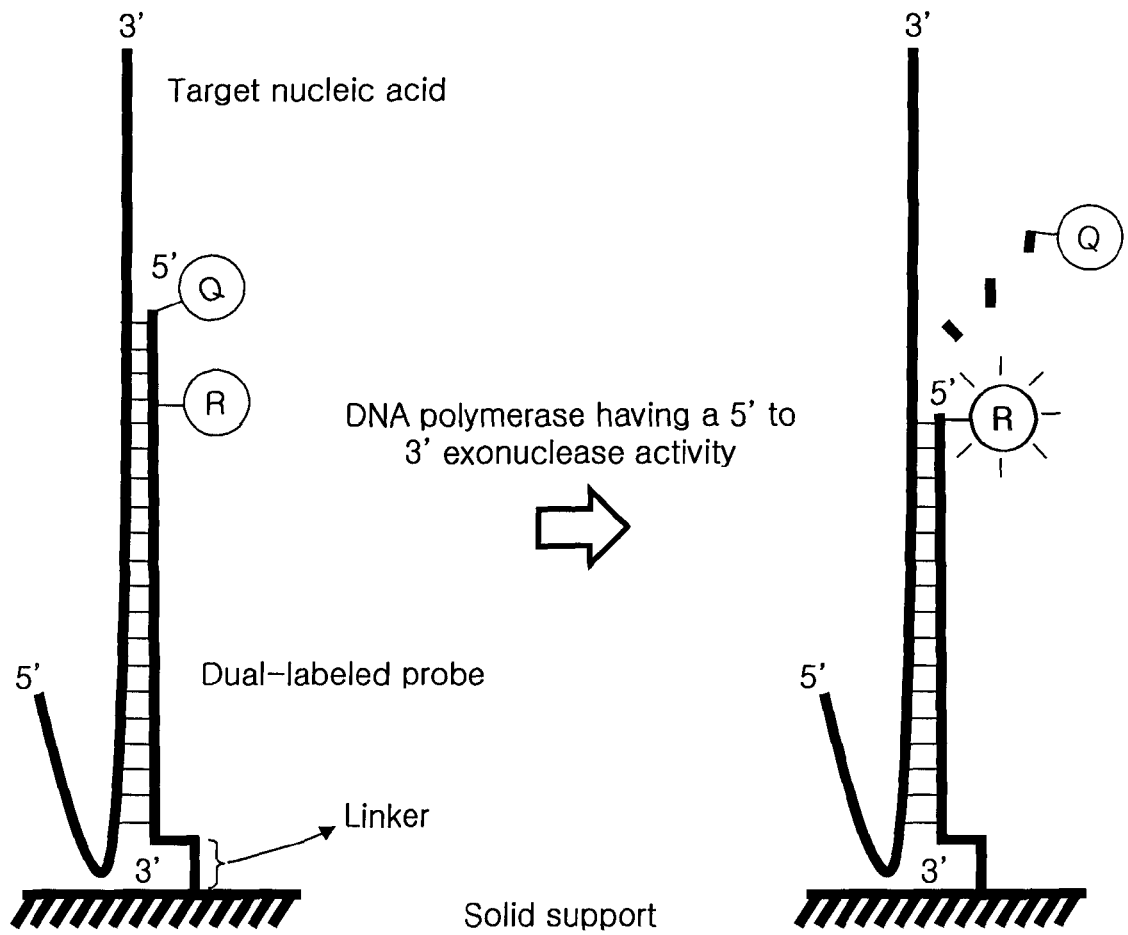

Fig. 2

*Taq* DNA polymerase

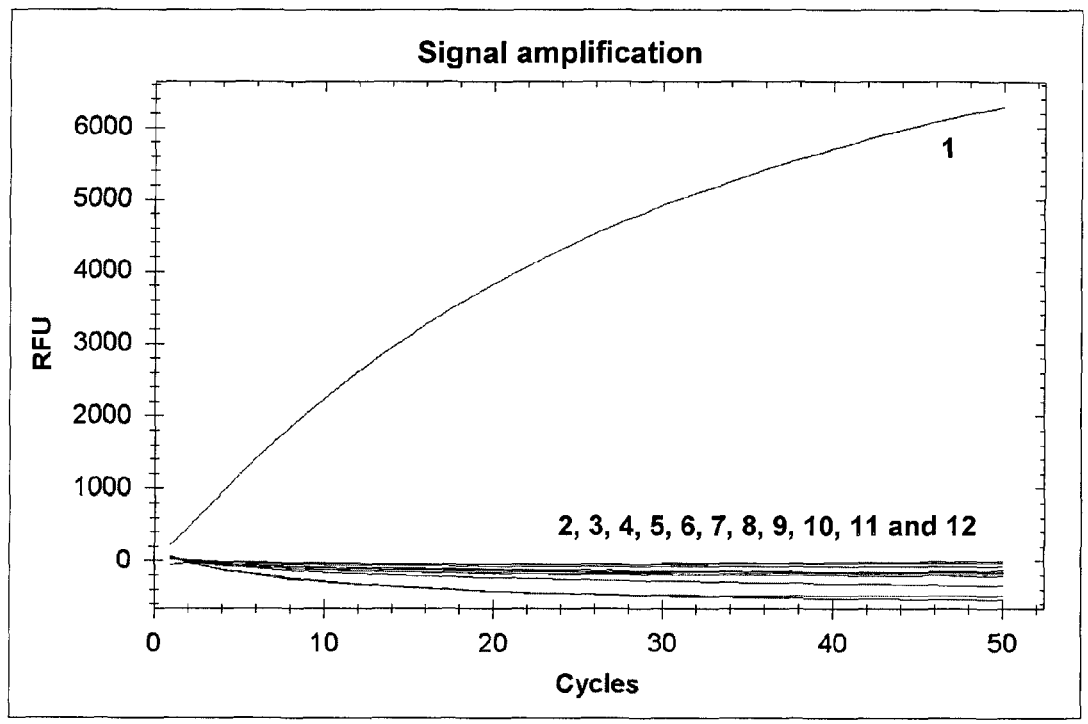

| No. | Template [1] | Probe [2] | No. | Template [1] | Probe [2] |
|---|---|---|---|---|---|
| 1 | + | SA_Con_M0 | 7 | − | SA_Con_M0 |
| 2 | + | SA_Con_D0(dT) | 8 | − | SA_Con_D0(dT) |
| 3 | + | SA_Con_D1(dT) | 9 | − | SA_Con_D1(dT) |
| 4 | + | SA_Con_D3(dT) | 10 | − | SA_Con_D3(dT) |
| 5 | + | SA_Con_D5(dT) | 11 | − | SA_Con_D5(dT) |
| 6 | + | SA_Con_D8(dT) | 12 | − | SA_Con_D8(dT) |

[1] Template is a synthetic oligonucleotide for *Staphylococcus aureus* gene.
[2] Probe has a fluorescent reporter molecule at its 5′-end portion and a quencher molecule at its 3′-end; the number in the probe name represents the position of a nucleotide having the fluorescent reporter molecule from the 5′-end nucleotide; (dT) represents that a thymine is linked with a fluorescent reporter molecule.

Fig. 3

*Tth* DNA polymerase

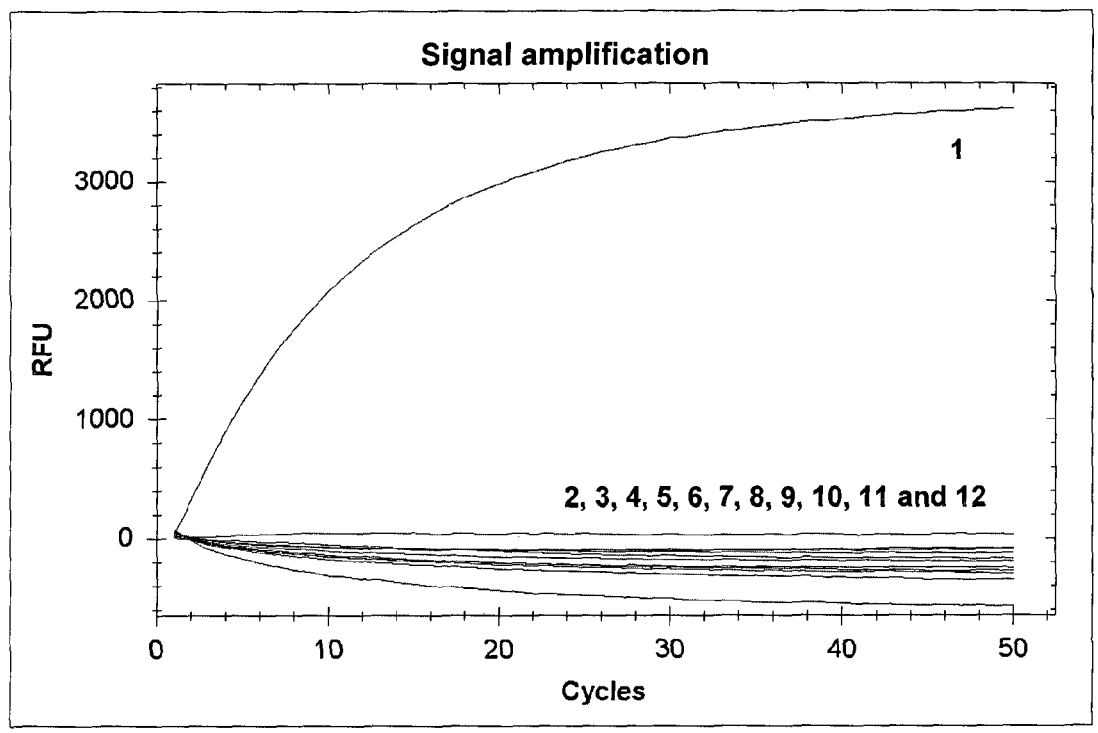

| No. | Template [1] | Probe [2] | No. | Template [1] | Probe [2] |
|---|---|---|---|---|---|
| 1 | + | SA_Con_M0 | 7 | − | SA_Con_M0 |
| 2 | + | SA_Con_D0(dT) | 8 | − | SA_Con_D0(dT) |
| 3 | + | SA_Con_D1(dT) | 9 | − | SA_Con_D1(dT) |
| 4 | + | SA_Con_D3(dT) | 10 | − | SA_Con_D3(dT) |
| 5 | + | SA_Con_D5(dT) | 11 | − | SA_Con_D5(dT) |
| 6 | + | SA_Con_D8(dT) | 12 | − | SA_Con_D8(dT) |

[1] Template is a synthetic oligonucleotide for *Staphylococcus aureus* gene.
[2] Probe has a fluorescent reporter molecule at its 5'-end portion and a quencher molecule at its 3'-end; the number in the probe name represents the position of a nucleotide having the fluorescent reporter molecule from the 5'-end nucleotide; (dT) represents that a thymine is linked with a fluorescent reporter molecule.

Fig. 4

Tfl DNA polymerase

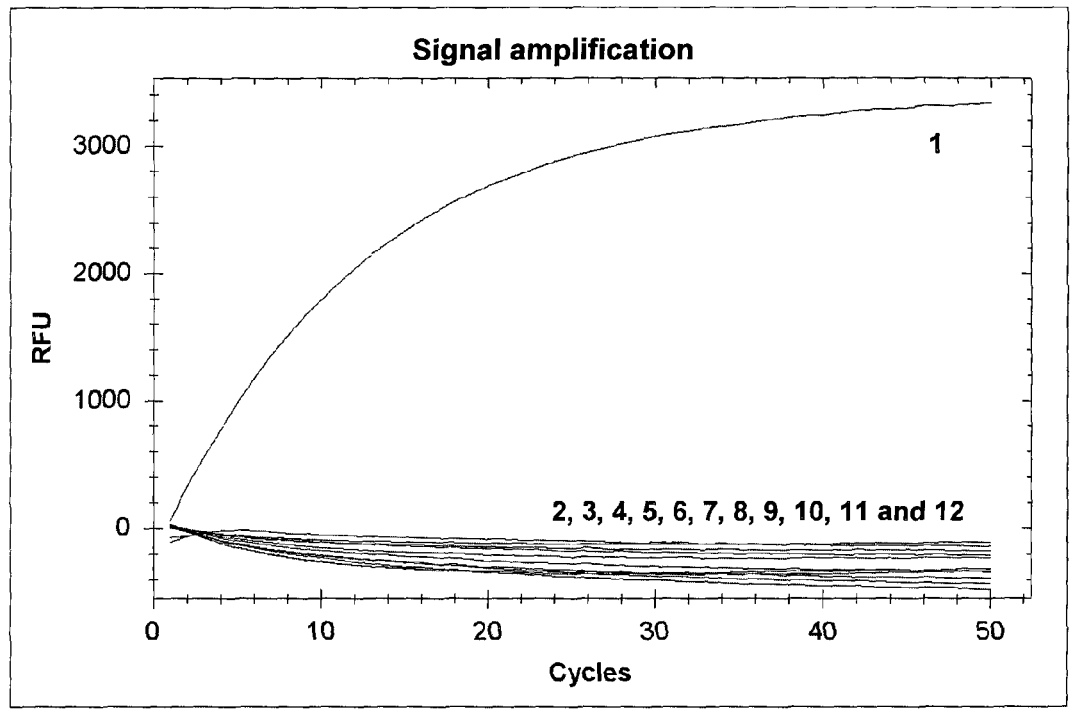

| No. | Template [1] | Probe [2] | No. | Template [1] | Probe [2] |
|---|---|---|---|---|---|
| 1 | + | SA_Con_M0 | 7 | − | SA_Con_M0 |
| 2 | + | SA_Con_D0(dT) | 8 | − | SA_Con_D0(dT) |
| 3 | + | SA_Con_D1(dT) | 9 | − | SA_Con_D1(dT) |
| 4 | + | SA_Con_D3(dT) | 10 | − | SA_Con_D3(dT) |
| 5 | + | SA_Con_D5(dT) | 11 | − | SA_Con_D5(dT) |
| 6 | + | SA_Con_D8(dT) | 12 | − | SA_Con_D8(dT) |

[1] Template is a synthetic oligonucleotide for *Staphylococcus aureus* gene.
[2] Probe has a fluorescent reporter molecule at its 5'-end portion and a quencher molecule at its 3'-end; the number in the probe name represents the position of a nucleotide having the fluorescent reporter molecule from the 5'-end nucleotide; (dT) represents that a thymine is linked with a fluorescent reporter molecule.

Fig. 5

Fluorescent image on microarray

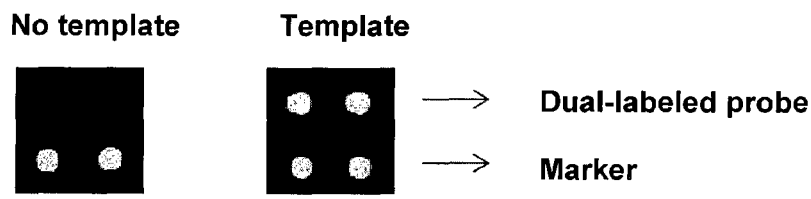

Fluorescent intensity on microarray

| Template [1] | Dual-labeled probe [2] | RFU [3] |
|---|---|---|
| - | SA-Con-M | 7,013 (±38.9) |
| + | SA-Con-M | 65,486 (±0.7) |

[1] Template is a synthetic oligonucleotide for *Staphylococcus aureus* gene.
[2] Dual-labeled probe has a quencher molecule at its 5'-end and a fluorescent reporter molecule linked to the base of an internal nucleotide.
[3] RFU represents Relative Fluorescent Units.

Fig. 6

Fluorescent image on microarray

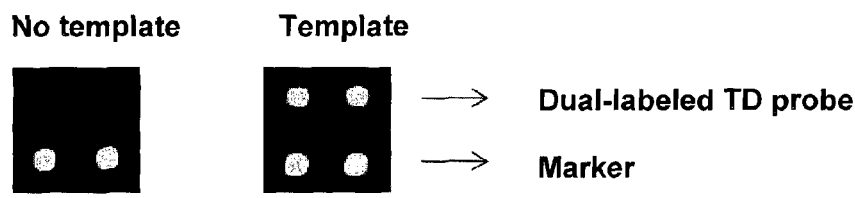

→ Dual-labeled TD probe
→ Marker

Fluorescent intensity on microarray

| Template [1] | Dual-labeled TD probe [2] | RFU [3] |
|---|---|---|
| - | SA-TD-M | 6,740 (±161.9) |
| + | SA-TD-M | 65,486 (±0.0) |

[1] Template is a synthetic oligonucleotide for *Staphylococcus aureus* gene.
[2] Dual-labeled TD probe has a quencher molecule at its 5'-end and a fluorescent reporter molecule linked to the base of an internal nucleotide located on its 5'-second hybridization portion.
[3] RFU represents Relative Fluorescent Units.

DETECTION OF TARGET NUCLEIC ACID SEQUENCES USING DUAL-LABELED IMMOBILIZED PROBES ON SOLID PHASE

CROSS-REFERENCE TO RELATED APPLICATIONS

This application is the U.S. national stage filing under 35 U.S.C. § 371 of International Application No. PCT/KR2011/007855, filed Oct. 20, 2011, which claims priority from Korean Patent Application 10-2010-0103599, filed Oct. 22, 2010.

BACKGROUND OF THE INVENTION

Field of the Invention

The present invention relates to a novel method for detection of target nucleic acid sequences on a solid phase using dual-labeled immobilized probes and its resistance to a 5' to 3' exonuclease activity of a DNA polymerase.

Description of the Related Art

DNA-based microarray technologies are highlighted as promising tools for ana lyzing the presence, level or expression patterns of a gene or a gene population (Schena et al., 1995. Quantitative Monitoring of Gene Expression Patterns with a Complementary DNA Microarray, *Science*, 270:467-470; DeRisi et al., 1996, Use of a cDNA Microarray to Analyse Gene Expression Patterns in Human Cancer, *Nature Genetics* 14:457-460).

The conventional DNA microarrays generally detect target sequences by hybridizing labeled target sequences with probes immobilized on solid substrates and measuring signal from the labels. However, the direct labeling of target sequences is considered cost- and time-ineffective and likely to affect level of target sequences.

To overcome shortcomings of conventional DNA microarray technologies, molecular beacon probes rather than using labeled target sequences have been suggested (Steemers et al., *Nat Biotechnol*, 18:91-94 (2000); Kim et al., *Biosensors Bioelectronics*, 22:1041-1047 (2007)). The molecular beacon probe technology using FRET phenomenon enables to detect target sequences in a real-time manner because a fluorescent signal is generated only when the probe is hybridized with target sequences.

However, a lot of methods depending heavily on hybridization with target sequences have serious problems of false positive data due to cross reactions (hybridizations), demanding improvement in reliability of final hybridization signals.

Besides hybridization processes using dual-labeled probes immobilized, several approaches using additional exonclease reactions, for example, a TaqMan probe method on a solid phase, have been suggested (Liu et al., Nucleic Acid Res. 34:e4 (2006)). Liu et al. used dual-labeled probes immobilized on a solid substrate in which a quencher molecule is linked to their 5'-end and a fluorescent reporter molecule to their 3'-end. The probes are digested by 5' to 3' nuclease activity of DNA polymerases during extension reaction of upstream primers. After the digestion reaction, the quencher molecule is released and the fluorescent reporter molecule is remained on the solid substrate, and target sequences are finally detected by measuring fluorescent signals on the solid substrate. The TaqMan probe array method using primer-dependent 5' to 3' nuclease activity as well as hybridization improves target specificity on a solid phase and enables to detect target sequences in a real-time manner.

However, the primer-dependent 5' to 3' nuclease activity of DNA polymerases in the TaqMan probe array method is likely to digest a nucleotide labeled with the fluorescent reporter molecule and therefore the fluorescent reporter molecule may not be remained on the solid substrate. To overcome such problem, the dual-labeled probe is designed such that the fluorescent reporter molecule is located on an uncleaved portion by the primer-dependent 5' to 3' nuclease activity of DNA polymerases. The uncleaved portion on the probe may be given by denaturation of a shorter probe digested during cleaved reaction from target nucleic acid sequences. To this end, the fluorescent reporter molecule is located at the 3'-end.

Therefore, in the TaqMan probe array method, the distance between the quencher and the fluorescent reporter molecule becomes longer. Longer is the distance of the dual label on probes, lower is a quenching efficiency of the dual label system. The lower quenching efficiency is responsible for generation of different background signals on spots from each other, finally giving false results.

Furthermore, since the TaqMan probe array method utilizes primer-dependent 5' to 3' nuclease activity of DNA polymerases, it needs upstream primers. The limitations associated with use of additional oligonucleotides (upstream primers) make it difficult to establish reaction conditions on microarray for multiplex target detection, which is considered one of factors to generate false positive results.

In the meantime, WO 2008/011004 discloses a target detection method using primer-independent cleavage activity of DNA polymerases in Linear-After-The-Exponential PCR (LATE-PCR). Unlike to TaqMan probe-based methods using primer-dependent 5' to 3' nuclease activity of DNA polymerases, the primer-independent 5' to 3' nuclease activity of DNA polymerases in WO 2008/011004 is induced with no help of primers. Furthermore, WO 2008/011004 discloses that linkage of labels to the 5'-end of probes via more than three methylene ($CH_2$) groups renders probes to be cleaved by the primer-independent 5' to 3' nuclease activity of DNA polymerases in more effective manner, while linkage of labels to the 5'-end of probes not using methylene ($CH_2$) chain renders probes to be resistant to primer-independent 5' to 3' nuclease activity of DNA polymerases.

The reactions using the susceptibility or resistance to primer-independent 5' to 3' nuclease activity of DNA polymerases controllable by modification of probes with no help of primers become applicable to target detection on a solid phase by further researches and developments.

There remain long-felt needs in the art to overcome shortcomings associated with conventional microarray methods and develop novel DNA microarray technologies for detecting a target sequence, preferably a multiple of target sequences on a microarray in a more convenient, reliable and reproducible manner. Furthermore, a novel real-time microarray method to perform reactions and detect signals on a solid phase in a real-time manner is also needed in the art for quantitative analysis of target nucleic acid sequences.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

Under such circumstances, the present inventor has made intensive researches to develop novel target detection technologies using probes with an interactive dual label for detection, identification and quantification of target nucleic acid sequences on a solid phase with no false positive and negative results in more convenient manner. The present inventor has variously tuned linking positions and patterns of labels on dual-labeled probes. Interestingly, the present inventor has found the resistance of a base-labeled nucleotide to a primer-independent 5' to 3' nuclease activity of DNA polymerases and has found a well-adaptable linking positions and patterns of labels on dual-labeled probes for detection of target nucleic add sequences in which a first label from a dual label is linked to the 5'-end of probes and the second label is linked to a base of a nucleotide placed downstream of the first label. The unique labeling fashion of the present invention permits probes to have resistance to a 5' to 3' exonuclease activity of a DNA polymerase as well as induces signal production (including signal generation, increase or decrease) depending on the presence of target nucleic acid sequences.

The internally blocked dual-labeled probes of the present invention allow to freely determine position of an internal label (i.e. the second label) and give signals from labels finally remained on a solid substrate in a reproducible manner with no false positive and negative data. We believe that the present invention provides the most optimal protocol using probes for detection of target nucleic acid sequences on a solid substrate.

Accordingly, it is an object of this invention to provide a method for detection of target nucleic acid sequences on a solid phase using resistance to a 5' to 3' exonuclease activity of a DNA polymerase.

It is another object of this invention to provide a kit for detecting a target nucleic acid sequence from a DNA or a mixture of nucleic acids on a solid phase using resistance to a 5' to 3' exonuclease activity of a DNA polymerase.

It is still another object of this invention to provide a method for conferring resistance to a 5' to 3' exonuclease activity of a DNA polymerase to an oligonucleotide.

Other objects and advantages of the present invention will become apparent from the detailed description to follow taken in conjugation with the appended claims and drawings.

BRIEF DESCRIPTION OF THE DRAWINGS

FIG. 1 schematically represents the process of the present invention.

FIGS. 2-4 represent the results of resistance to 5' to 3' exonuclease activity of several DNA polymerases conferred by the linkage of a label to a base component of an nucleotide of probes. In FIGS. 2-4, Taq DNA polymerase, Tth DNA polymerase and Tfl DNA polymerases are used, respectively.

FIG. 5 represent the results of detection of target nucleic acid sequences using resistance to 5' to 3' exonuclease activity of DNA polymerase with a dual-labeled probe on microarray. The dual-labeled probes having conventional structure were used.

FIG. 6 represent the results of detection of target nucleic acid sequences using resistance to 5' to 3' exonuclease activity of DNA polymerase with a dual-labeled probe on microarray. The dual-labeled probes having the mDSO (modified dual specificity oligonucleotide) structure were used.

DETAILED DESCRIPTION OF THIS INVENTION

The present invention is directed to target detection methods using peculiar resistance to a primer-independent 5' to 3' exonuclease activity of a DNA polymerase that is conferred by linking labels to a base of nucleotides of probes oligonucleotides.

In one aspect of this invention, there is provided a method for detecting a target nucleic acid sequence from a DNA or a mixture of nucleic acids on a solid phase using a dual-labeled probe with resistance to a 5' to 3' exonuclease activity of a DNA polymerase, comprising:

(a) hybridizing the target nucleic acid sequence with an immobilized probe having a nucleotide sequence complementary to the target nucleic acid sequence;

wherein the probe immobilized on a solid substrate through its 3'-end has an interactive dual label comprising a reporter molecule and a quencher molecule; the interactive dual label is positioned on the immobilized probe to induce energy quenching between the reporter molecule and the quencher molecule; a first label and a second label are selected from the reporter molecule and the quencher molecule; the first label is linked to the 5'-end of the immobilized probe and the second label is linked to a base of a nucleotide placed downstream of the first label, such that the linkage of the second label permits the nucleotide to have resistance to the 5' to 3' exonuclease activity of the DNA polymerase;

(b) contacting the resultant of step (a) to the DNA polymerase having the 5' to 3' exonuclease activity under conditions for cleavage of the immobilized probe; wherein the immobilized probe hybridized with the target nucleic acid sequence is digested by an exonucleolytic reaction of the DNA polymerase to release the first label from the immobilized probe, resulting in change in a signal on the solid substrate;

(c) terminating the exonucleolytic reaction of the DNA polymerase at the nucleotide labeled with the second label; wherein the termination of the exonucleolytic reaction is induced by resistance of the nucleotide having the base linked with the second label; wherein the second label is remained on the solid substrate; and (d) detecting the signal change on the solid substrate, such that the signal change by the cleavage of the immobilized probe is indicative of the presence of the target nucleic acid sequence.

The present inventor has made intensive researches to develop novel target detection technologies using probes with an interactive dual label for detection, identification and quantification of target nucleic acid sequences on a solid phase with no false positive and negative results in more convenient manner. The present inventor has variously tuned linking positions and patterns of labels on dual-labeled probes. Interestingly, the present inventor has found the resistance of a base-labeled nucleotide to a primer-independent 5' to 3' nuclease activity of DNA polymerases and found a well-adaptable linking positions and patterns of labels on dual-labeled probes for detection of target nucleic acid sequences in which a first label from a dual label is linked to the 5'-end of probes and the second label is linked to a base of a nucleotide placed downstream of the first label.

The unique labeling fashion of the present invention permits probes to have resistance to a 5' to 3' exonuclease activity of a DNA polymerase as well as induces signal production (including signal generation, increase or decrease) depending on the presence of target nucleic acid sequences.

The internally blocked dual-labeled probes of the present invention allow to freely determine position of an internal label (i.e. the second label) and give signals from labels finally remained on a solid substrate in a reproducible manner with no false positive and negative data. We believe that the present invention provides the most optimal protocol using probes for detection of target nucleic acid sequences on a solid substrate.

The present inventor has intensively researched to control the primer-independent 5' to 3' exonuclease activity of DNA polymerases, and interestingly found that a nucleotide having a label linked to its base has resistance to a primer-independent 5' to 3' exonuclease activity of DNA polymerases.

Based on the findings, the present inventor has established a novel approach to confer resistance to the primer-independent 5' to 3' exonuclease activity of DNA polymerases to oligonucleotides.

Furthermore, the present inventor has adopted such findings to dual-labeled probes immobilized on probes, thereby establishing a novel target detection method using dual-labeled probes on solid phase with no limitation of label positions. To the best of our knowledge, this approach is first suggested by the present inventor, ensuring to detect target nucleic acid sequences in more effective and accurate manner.

In conventional solid phase methods using cleavage reaction of dual-labeled probes, target nucleic acid sequences may be detected only when a label linked to an internal nucleotide on probes is remained on a solid substrate in the cleavage reaction. In TaqMan probe-based methods using primer-dependent 5' to 3' nuclease activity of DNA polymerases, the shorter probes in the cleavage reaction are likely to be denatured from target nucleic acid sequences, which is dependent on probe sequences and reaction conditions, resulting in formation of an uncleaved portion on the probes. Therefore, where a label is positioned on the uncleaved portion on the probes, the label may be finally remained on the solid substrate. However, such methods have serious shortcomings in which the label linked to the internal nucleotide on probes has to be positioned on the uncleaved portion in considering reaction conditions. Due to the limitation, dual-labeled probes have to be designed such that a dual label is significantly separated. Longer is the distance of the dual label on probes, lower is a quenching efficiency of the dual label system. The lower quenching efficiency is responsible for generation of different background signals on spots from each other, finally giving false results.

The present invention allows to detect target nucleic acid sequences using dual-labeled probes on a solid phase with overcoming problems of conventional methods described above. In accordance with the present invention, the linkage of labels to a base of an internal nucleotide of probes renders the internal nucleotide to be resistant to the primer-independent 5' to 3' exonuclease activity of DNA polymerases. The probe immobilized on a solid substrate is subject to cleavage reactions of DNA polymerases and the label linked to the base of the internal nucleotide is remained on the solid substrate due to the resistance. Unlike to TaqMan probe-based methods using primer-dependent 5' to 3' nuclease activity of DNA polymerases, the present invention ensures to freely determine the position of the internal label on probes with no considering uncleaved portions that is dependent on reaction conditions, and minimize background signal by positioning labels at a site suitable to maximize quenching efficiency of the dual label system on probes.

Preferably, the immobilized probes used in this invention are immobilized via its 3'-end on the solid substrate. One of the interactive dual label is linked to a structure of a nucleotide except for a base at the 5'-end of the immobilized probe via a carbon spacer and the other is linked to a base of an internal nucleotide. In accordance with the present invention, the immobilized probe hybridized with the target nucleic acid sequence is progressively cleaved at its 5'-end in a 5' to 3-direction by the primer-independent 5' to 3' exonuclease activity of DNA polymerases to release the label at its 5'-end. When the enzyme encounters to the internal nucleotide labeled at its base component, the cleavage reaction is terminated due to the resistance and the label to the internal nucleotide is finally remained in the solid substrate.

In general, the 5' to 3' exonuclease activity of DNA polymerases is classified into an upstream oligonucleotide-dependent activity and an upstream oligonucleotide-independent activity. The upstream oligonucleotide includes primers, extended product of primers and probes positioned upstream of oligonucleotides to be cleaved. Because the present invention employs the upstream oligonucleotide-independent activity, the term used herein "5' to 3' exonuclease activity of DNA polymerases" refers to upstream oligonucleotide-independent 5' to 3' exonuclease activity of DNA polymerases, unless otherwise indicated.

The present invention will be described in more detail as follows:

In accordance with the present invention, the target nucleic acid sequence is hybridized with the dual-labeled probe immobilized on the solid substrate.

The term used herein "target nucleic acid", "target nucleic acid sequence" or "target sequence" refers to a nucleic acid sequence of interest for detection, which is annealed to or hybridized with a probe or a primer under hybridization, annealing or amplifying conditions.

The term used herein "probe" refers to a single-stranded nucleic acid molecule comprising a portion or portions that are substantially complementary to a target nucleic acid sequence. Preferably, the probe is a single-stranded deoxyribonucleotide molecule. The probes may also include ribonucleotides.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH. The primer is preferably single stranded for maximum efficiency in amplification. Preferably, the primer is an oligodeoxyribonucleotide.

The probes and primers used in this invention may be comprised of naturally occurring dNMP (i.e., dAMP, dGM, dCMP and dTMP), modified nucleotide, or non-natural nucleotide. The modified nucleotide or non-natural nucleotide may contain modified or non-natural bases.

The primer must be sufficiently long to prime the synthesis of extension products in the presence of the agent for polymerization. The exact length of the primers will depend on many factors, including temperature, application, and source of primer. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

The term used "hybridizing" used herein refers to the formation of a double-stranded nucleic acid from complementary single stranded nucleic acids. The hybridization may occur between two nucleic acid strands perfectly matched or substantially matched with some mismatches. The complementarity for hybridization may depend on hybridization conditions, particularly temperature.

There is no intended distinction between the terms "annealing" and "hybridizing", and these terms will be used interchangeably.

The immobilized probes used in this invention have a nucleotide sequence complementary to target nucleic acid sequences. The term "complementary" is used herein to mean that primers or probes are sufficiently complementary to hybridize selectively to a target nucleic acid sequence under the designated annealing conditions or stringent conditions, encompassing the terms "substantially complementary" and "perfectly complementary", preferably perfectly complementary.

The immobilized probes used in this invention are immobilized via its 3'-end on the solid substrate. A preferable solid substrate includes suitable solid or semi-solid supporters, such as membrane, filter, chip, slide, wafer, fiber, magnetic or nonmagnetic bead, gel, tubing, plate, macromolecule, microparticle and capillary tube. In many embodiments, at least one surface of the solid substrate will be substantially flat, although in some embodiments it may be desirable to physically separate synthesis regions for different compounds with, for example, wells, raised regions, pins, etched trenches, or the like. According to other embodiments, the solid substrate(s) will take the form of beads, resins, gels, microspheres, or other geometric configurations.

Preferably, the solid substrate comprises a microarray. The probes may be immobilized directly or indirectly (preferably indirectly) onto the surface of the solid substrate. Furthermore, the probes may be immobilized on the surface of the solid substrate in a covalent or non-covalent manner. Where the probes are immobilized indirectly onto the surface of the solid substrate, suitable linkers may be used. The linkers useful in this invention may include any linkers utilized for probe immobilization on a microarray. For example, alkyl or aryl compounds with amine functionality, or alkyl or aryl compounds with thiol functionality serve as linkers for probe immobilization. In addition, a poly (T) tail or a poly (A) tail may be used as linkers for increasing hybridization efficiency and decreasing space hindrance which is very likely to inhibit enzymatic actions (e.g., enzymatic cleavage reactions). The poly (T) tail or a poly (A) tail is considered not to be contained in sequences of probes.

The immobilized probes used in this invention have an interactive dual-label system comprising a reporter molecule and a quencher molecule.

The interactive label system is a signal generating system in which energy is passed non-radioactively between a donor molecule (reporter molecule) and an acceptor molecule (quencher molecule).

As a representative of the interactive label system, the FRET (fluorescence resonance energy transfer) label system includes a reporter molecule (donor molecule) and a quencher molecule (acceptor molecule). In FRET, the energy donor is fluorescent, but the energy acceptor may be fluorescent or non-fluorescent.

In another form of interactive label systems, the energy donor is non-fluorescent, e.g., a chromophore, and the energy acceptor is fluorescent. In yet another form of interactive label systems, the energy donor is luminescent, e.g. bioluminescent, chemiluminescent, electrochemiluminescent, and the acceptor is fluorescent.

More preferably, the signal indicative of the target nucleic acid sequence is generated by interactive label systems, most preferably the FRET label system.

The reporter molecule and the quencher molecule useful in the probe may include any molecules known in the art. Examples of those are: Cy2™ (506), YO-PRO™-1 (509), YOYO™-1 (509), Calcein (517), FITC (518), FluorX™ (519), Alexa™ (520), Rhodamine 110 (520), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), DiI (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red (615), Nile Red (628), YO-PRO™-3 (631), YOYO™-3 (631), R-phycocyanin (642), C-Phycocyanin (648), TO-PRO™-3 (660), TOTO3 (660), DiD DiIC (5) (665), Cy5™ (670), Thiadicarbocyanine (671), Cy5.5 (694), HEX (556), TET (536), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705) and Quasar 705 (610). The numeric in parenthesis is a maximum emission wavelength in nanometer.

Suitable pairs of reporter-quencher are disclosed in a variety of publications as follows: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, $2^{nd}$ Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. R, Handbook of Fluorescent Probes and Research Chemicals, $6^{th}$ Edition (Molecular Probes, Eugene, Oreg., 1996) U.S. Pat. Nos. 3,996,345 and 4,351,760.

The reporter and quencher molecules each may be fluorescent. Also, the reporter molecule may be fluorescent, but the quencher molecule may be non-fluorescent. For example, a non-fluorescent dark quencher capable of quenching a fluorescence of a wide range of wavelengths or a specific wavelength may be used in this invention. Where the quencher molecule may be fluorescent, the target nucleic acid sequence may be detected from signal change in the fluorescent quencher molecule.

In the dual-label system on the immobilized probes, the reporter encompasses a donor of FRET and the quencher encompasses the other partner (acceptor) of FRET. For example, a fluorescein dye is used as the reporter and a rhodamine dye as the quencher.

The reporter molecule and quencher molecule may be linked to probes according to conventional methods. For instance, the reporter molecule and quencher molecule may be linked to probes through spacers having at least three carbon atoms (e.g., 3-carbon spacer, 6-carbon spacer, 9-carbon spacer and 12-carbon spacer).

In the immobilized probes used in this invention, the first label selected from the reporter molecule and the quencher molecule is linked to the 5'-end of the immobilized probe and the second label selected from the reporter molecule and the quencher molecule is linked to a base of a nucleotide placed downstream of the first label.

Preferably, the first label to the 5'-end of the immobilized probe may be linked directly or indirectly (e.g., via a linker) to a phosphate group of the 5'-end. Alternatively, the first label may be linked to a ribose of the 5'-end, preferably to a 5-carbon of the ribose.

The second label on the immobilized probe is linked to a base of a nucleotide placed downstream of the first label. The second label may be linked to adenine, guanine, cytosine or thyamine, preferably thyamine.

It is preferable that the labeling of the base by the second label is made at a position not involved in hydrogen bonds. For example, the second label may be linked to a 5-carbon or 6-carbon of thyamine, preferably a methyl group of 5-carbon of thyamine.

Interestingly, the present inventor has discovered that the labeling of a base by the second label confers to the labeled nucleotide resistance to a 5' to 3' exonuclease activity of a DNA polymerase.

The term used herein "resistance" means that little or no, preferably no cleavage of a nucleotide molecule by a 5' to 3' exonuclease activity of a DNA polymerase occurs.

According to a preferred embodiment, the first label is the quencher molecule and the second label is the reporter molecule. Alternatively, the first label is the reporter molecule and the second label is the quencher molecule.

The first and second labels used in this invention provide an interactive dual label system. The dual label is located at sites of the immobilized probes such that energy quenching occurs between the dual label, in particular, when the immobilized probes are not hybridized with nucleic acid sequences in samples to be analyzed.

For energy quenching, the dual label is located on probes in a certain distance or in a three-dimensional structure (e.g., random coil or hairpin structure). The immobilized probe hybridized with the target nucleic acid sequence is progressively cleaved at its 5'-end in a 5' to 3-direction by the 5' to 3' exonuclease activity of DNA polymerases to release the first label at its 5'-end. Finally, the second label is remained in the solid substrate and energy quenching between the first and second labels does no longer occur, resulting in signal change (signal generation, extinguishment, increase or decrease) to indicating the presence of the target nucleic acid sequence.

Where the first label is the quencher molecule and the second label is the reporter molecule, the 5'-end of the immobilized probe is cleaved upon exonucleolytic reaction to release the first label while the second label is remained on the solid substrate. The signal from the reporter molecule as the second label is measured to detect the target nucleic acid sequence.

Where the first label is the reporter molecule and the second label is the quencher molecule, the 5'-end of the immobilized probe is cleaved upon exonucleolytic reaction to release the first label while the second label is remained on the solid substrate. Where the quencher molecule is fluorescent, the quencher remained on the solid substrate generates different fluorescent signal from an initial signal before release of the first label, thereby detecting the target nucleic acid sequence. The signal from the reporter molecule as the second label is measured to detect the target nucleic acid sequence.

The most prominent advantage of the present invention is to determine the position of the internal label with no limitation. The internal label may be positioned at any site apart from the 5'-end of the immobilized probe because of the internal label-caused resistance to the 5' to 3' exonuclease activity of the DNA polymerase. Preferably, the internal label is positioned at a site sufficient to maximize quenching efficiency of the dual label.

According to a preferred embodiment, the first label and the second label are separated from each other to an extent that the 5' to 3' exonuclease activity of the DNA polymerase acts on sites between them.

According to a preferred embodiment, the second label is separated from the first label by a cleavage site on the immobilized probe by the 5' to 3' exonuclease activity.

According to a preferred embodiment, the second label is located at a suitable site to terminate the cleavage reaction due to the resistance under given reaction conditions.

Preferably, the second label is located at least 2 nucleotides, more preferably at least 3 nucleotides, still more preferably at least 4 nucleotides apart from the first label.

Preferably, the second label is located 2-25 nucleotides, 2-20 nucleotides, 2-15 nucleotides, 3-25 nucleotides, 3-20 nucleotides, 3-15 nucleotides, 4-25 nucleotides, 4-20 nucleotides or 4-15 nucleotides apart from the first label.

According to a preferred embodiment, the second label is not located at a portion that is uncleaved due to denaturation of the probe cleaved from the target nucleic acid sequence. The reason for those is that the uncleaved portion is dependent on either reaction conditions or probe sequence that becomes determinant factors for position of the second label.

According to a preferred embodiment, the second label is located at least 10 nucleotides, more preferably at least 15 nucleotides, still more preferably at least 20 nucleotides and still further more preferably at least 25 nucleotides apart from the 3'-end of the immobilized probe.

The present invention does not require that target nucleic acid sequences to be detected have any particular sequence or length, including any DNA (gDNA and cDNA) and RNA molecules. Where a mRNA is employed as starting material, a reverse transcription step is necessary prior to performing annealing step, details of which are found in Joseph Sambrook, et al., Molecular Cloning, A Laboratory Manual, Cold Spring Harbor Laboratory Press, Cold Spring Harbor, N.Y. (2001); and Noonan, K. F. et al., Nucleic Acids Res. 16:10366 (1988). For reverse transcription, a random hexamer or an oligonucleotide dT primer hybridizable to mRNA can be used. The target nucleic acid sequences which may be detected include any naturally occurring prokaryotic, eukaryotic (for example, protozoans and parasites, fungi, yeast, higher plants, lower and higher animals, including mammals and humans) or viral (for example, Herpes viruses, HIV, influenza virus, Epstein-Barr virus, hepatitis virus, polio virus, etc.) or viroid nucleic acid.

The annealing or hybridization of probes or primers may be a wide variety of hybridization processes known to those of skill in the art. The suitable hybridization conditions in the present invention may be routinely determined by optimization procedures. Conditions such as temperature, concentration of components, hybridization and washing time, buffer components, and their pH and ionic strength may be varied depending on various factors, including the length and GC content of oligonucleotides such as probes and target nucleic acid sequences. The detailed conditions for hybridization can be found in Joseph Sambrook, et al., *Molecular Cloning, A Laboratory Manual*, Cold Spring Harbor Laboratory Press, Cold Spring Harbor, N.Y. (2001); and M. L. M. Anderson, *Nucleic Acid Hybridization*, Springer-Verlag New York Inc. N.Y. (1999).

For example, the hybridization temperature of the immobilized probe with target nucleic acid sequence ranges from about 40° C. to 80° C., more preferably 45° C. to 75° C., still more preferably 50° C. to 72° C.

Following the hybridization reaction, the resultant of step (a) is contacted to the DNA polymerase having the 5' to 3' exonuclease activity under conditions for cleavage of the immobilized probe. The first label is released from the immobilized probe by the DNA polymerase having the 5' to 3' exonuclease, only when the immobilized probe is hybridized with the target nucleic acid sequence, finally inducing change in a signal on the solid substrate (see FIG. 1). The signal change is indicative of the presence of the target nucleic acid sequence.

The phrase "conditions for cleavage of the immobilized probe" means the reaction conditions for digestion of the immobilized probe by DNA polymerases having the 5' to 3' exonuclease activity, including temperature, pH, ionic strength, buffer, probe length and sequence, and types of exonucleases. For example, where Taq DNA polymerase is used, the conditions for cleavage of the immobilized probe include Tris-HCl buffer, KCl, $MgCl_2$ and temperature.

The DNA polymerase having the 5' to 3' exonuclease activity used in this invention include enzymes that catalyze an exonucleolytic reaction in a 5' to 3' direction by acting on probes involved in hybridization with target nucleic acid sequences.

The DNA polymerase having the 5' to 3' exonuclease activity used in this invention (e.g., *E. coli* DNA polymerase I, a thermostable DNA polymerase and bacteriophage 17 DNA polymerase) is preferably a thermostable DNA polymerase having the 5' to 3' exonuclease activity, including *Thermus aquaticus* (Taq), *Thermus thermophllus, Thermus filiformis, Thermus flavus, Thermus antranikianii, Thermus caldophilus, Thermus chliarophilus, Thermus igniterrae, Thermus lacteus, Thermus oshimai, Thermus ruber; Thermus rubens, Thermus scotoductus, Thermus silvans, Thermus* species Z05 and *Thermus* species sps 17

The immobilized probe hybridized with the target nucleic acid sequence is digested by the DNA polymerase having the 5' to 3' exonuclease activity to release the first label from the immobilized probe, thereby inducing change in a signal on the solid substrate.

After the exonucleolytic reaction of the immobilized probe by the DNA polymerase having the 5' to 3' exonuclease activity, it is terminated at the nucleotide labeled with the second label. The termination of the exonucleolytic reaction is induced by resistance of the nucleotide labeled with the second label and the second label is finally remained on the solid substrate.

Following the termination of the exonucleolytic reaction, the signal change (signal increase or decrease) on the solid substrate is detected, such that the signal change by the cleavage of the immobilized probe is indicative of the presence of the target nucleic acid sequence.

The signal may be detected or measured by conventional methods for each label. For example, the fluorescence signal may be detected or measured by conventional methods, e.g., fluorometers.

Finally, the signal change indicative of the presence of the target nucleic acid sequence is detected on the solid substrate. Preferably, the signal change by the cleavage of the immobilized probe is signal increase on the solid substrate.

The solid substrate, preferably, microarray, to provide a reaction environment in this invention may include any those known to one of skill in the art. All processes of the present invention, i.e., annealing to target nucleic acid, extension/digestion and fluorescence detection, are carried out on the microarray. The immobilized probes on the microarray serve as hybridizable array elements. The solid substrate to fabricate microarray include, but not limited to, metals (e.g., gold, alloy of gold and copper, aluminum), metal oxide, glass, ceramic, quartz, silicon, semiconductor, Si/SiO$_2$ wafer, germanium, gallium arsenide, carbon, carbon nanotube, polymers (e.g., polystyrene, polyethylene, polypropylene and polyacrylamide), sepharose, agarose and colloids. A plurality of immobilized probes in this invention may be immobilized on, an addressable region or two or more addressable regions on a solid substrate that may comprise 2-1,000,000 addressable regions. Immobilized probes may be fabricated to produce array or arrays for a given application by conventional fabrication technologies such as photolithography, ink-jetting, mechanical microspotting, and derivatives thereof.

Since the immobilized probes on the solid substrate are physically separated from one another, the present invention enables to simultaneously detect a multiple of target nucleic acid sequences on the solid substrate even when a single type of a dual label is used. In this regard, the number of target nucleic acid sequences to be detected by the present invention on the solid phase is not limited.

According to a preferred embodiment, the method further comprise repeating the steps (a)-(b) or (a)-(c) (preferably twice, more preferably at least five times and still more preferably at least ten times) with denaturation between repeating cycles.

Where the steps (a)-(b) or (a)-(c) are repeated, it is preferred that the present invention may further comprise the step of denaturation of the double strand of the target nucleic acid sequence to the single strand.

Where the steps (a)-(b) or (a)-(c) are repeated to induce cyclic exonucleolytic reaction, the extent of the signal change becomes greater depending on the amount of the target nucleic acid sequence, enabling quantification of the target nucleic acid sequence. Where the present invention is performed according to the cyclic exonucleolytic reaction, the detection of the step (d) may be performed at the end of the repetition (i.e., end-point manner), for each cycle of the repetition (i.e., real-time manner), or at each of predetermined time intervals during the repetition. The real-time detection is suitable to quantify the target nucleic acid sequence.

A washing step may be carried out prior to the step (d). However, the present invention can detect signals only present on the solid substrate using suitable devices such as confocal laser scanners without washing the solid substrate and with no interference with label molecules released from the dual-labeled probes on the solid substrate.

According to a preferred embodiment, the step (a) further comprises a reverse primer for producing copies of the target nucleic acid sequence to be hybridized with the immobilized probe. The addition production of the target nucleic acid sequence allows to generate stronger signal change.

For instance, at least two types of target nucleic acid sequences are multiplex-amplified using at least two types of amplification primers and hybridized with at least two types of immobilized probes, followed by extension and cleavage reactions using at least two types of reverse primers and the DNA polymerase having the 5' to 3' exonuclease activity, finally giving stronger signal change than reactions not using reverse primers.

According to a preferred embodiment, the immobilized probe has a modified dual specificity oligonucleotide (mDSO) structure. The mDSO structure possesses significantly higher target specificity than conventional probes (see WO 2011/028041).

According to a preferred embodiment, the immobilized probe is a target discriminative probe (TD probe) having a modified dual specificity oligonucleotide (mDSO) structure represented by the following general formula I to allow for discrimination of a target nucleic acid sequence from a non-target nucleic acid sequence:

$$5'\text{-}X'_p\text{—}Y'_q\text{—}Z'_r\text{-}3' \qquad (I)$$

wherein, $X'_p$ represents a 5'-second hybridization portion having a hybridizing nucleotide sequence complementary to the target nucleic acid sequence; $Y'_q$ represents a separation portion comprising at least three universal bases, $Z'_r$ represents a 3'-first hybridization portion having a hybridizing nucleotide sequence complementary to the target nucleic acid sequence; the TD probe has an interactive dual label comprising a reporter molecule and a quencher molecule; the interactive dual label is positioned on the immobilized probe to induce energy quenching between the reporter molecule and the quencher molecule; a first label and a second label are selected from the reporter molecule and the quencher molecule; the first label is linked to the 5'-end of the 5'-second hybridization portion and the second label is linked to a base of a nucleotide placed downstream of the first label; p, q and r represent the number of nucleotides; and X', Y' and Z' are deoxyribonucleotides or ribonucleotides; the $T_m$ of the 5'-second hybridization portion is lower than that of the 3'-first hybridization portion and the separation portion has the lowest $T_m$ in the three portions of $X'_p$, $Y'_q$ and $Z'_r$; the separation portion separates the 5'-second hybridization portion from the 3'-first hybridization portion in terms of hybridization events to the target nucleic acid sequence, whereby the hybridization specificity of the TD probe are determined dually by the 5'-second hybridization portion and the 3'-first hybridization portion such that the overall hybridization specificity of the TD probe is enhanced; wherein when the TD probe is hybridized with the target nucleic acid sequence, both of the 5'-second hybridization portion and the 3'-first hybridization portion are hybridized with the target nucleic acid sequence and the 5'-end of the 5'-second hybridization portion is digested by the exonucleolytic reaction of the DNA polymerase to release the first label from the TD probe, resulting in change in a signal on the solid substrate; the second label is remained on the solid substrate due to the resistance of the nucleotide having the base linked with the second label; wherein when the TD probe is hybridized with the non-target nucleic acid sequence, both of the 5'-second hybridization portion and the separation portion form a single strand and the 5'-second hybridization portion is not digested by the DNA polymerase, resulting in no change in the signal on the solid substrate, whereby the TD probe allows discriminating the target nucleic acid sequence from the non-target nucleic acid sequence and the signal change on the solid substrate is indicative of the presence of the target nucleic acid sequence.

The term used herein "target discriminative probe" means a probe having the mDSO structure and different hybridization patterns for target and non-target nucleic acid sequences to discriminate target nucleic acid sequences from non-target nucleic acid sequences.

The TD probe used in the present invention having the mDSO structure comprises (i) a hybridizing nucleotide sequence complementary to the target nucleic acid sequence; and (ii) a 5'-second hybridization portion and a separation portion pivotal to discrimation of target nucleic acid sequences from non-target nucleic acid sequences.

The mDSO structure is a newly modified version of a DSO (dual specificity oligonucleotide) structure that was first proposed by the present inventor (see WO 2006/095981). The DSO structure is also called DPO (dual priming oligonucleotide) as it serves as primers (Chun et al., Dual priming oligonucleotide system for the multiplex detection of respiratory viruses and SNP genotyping of CYP2C19 gene, *Nucleic Acid Research*, 35: 6e40 (2007)). The DSO embodies a novel concept in which its hybridization or annealing is dually determined by the 5'-high $T_m$ specificity portion (or the 5'-first hybridization portion, the 5'-first priming portion) and the 3'-low $T_m$ specificity portion (or the 3'-second hybridization portion, the 3'-second priming portion) separated by the separation portion, exhibiting dramatically enhanced hybridization specificity (see WO 2006/095981; Kim et al., Direct detection of lamivudine-resistant hepatitis B virus mutants by multiplex PCR using dual-priming oligonucleotide primers, Journal of Virological Methods, 149:76-84 (2008); Kim, et. al., Rapid detection and identification of 12 respiratory viruses using a dual priming oligonucleotide system-based multiplex PCR assay, Journal of Virological Methods, doi:10.1016/j.jviromet.2008.11.007 (2008); Horii et. al. Use of dual priming oligonucleotide system to detect multiplex sexually transmitted pathogens in clinical is specimens, Letters in Applied Microbiology, doi:10.111/j.1472-765X2009.02618x(2009)). As such, the DSO has eventually two segments with distinct hybridization properties: the 5'-first hybridization portion that initiates stable hybridization, and the 3'-second hybridization portion that mainly determines target specificity.

The mDSO structure is a reversal of the DSO structure: the 5'-second hybridization portion that mainly determines target specificity, and the 3'-first hybridization portion that initiates stable hybridization. Only when the 5'-second hybridization portion of the TD probe is completely hybridized with target nucleic acid sequences, the 5'-end of probes is cleaved by DNA polymerases having the 5' to 3' exonuclease activity, contributing to dramatic target specificity of the TD probe.

In the present invention, the TD probe is responsible partly for removal of false positive data in detection of target nucleic acid sequences, particularly, multiplex detection of target nucleic acid sequences, because it has distinctly different hybridization behaviors for each of target and non-target nucleic acid sequences.

When the TD probe is hybridized with a target nucleic acid sequence, both the 5'-second hybridization portion and the 3'-first hybridization portion of the TD probe form a double strand with the target nucleic acid sequence. Where the TD probe is hybridized with a non-target nucleic acid sequence (i.e., non-target hybridization or binding), its 3'-first hybridization portion prevailingly binds to the non-target nucleic acid sequence but both of the 5'-second hybridization portion and the separation portion are not hybridized with the non-target nucleic acid sequence such that both portions form a single strand.

Where the TD probe is hybridized with the target nucleic acid sequence, its 5'-second hybridization portion is digested by DNA polymerases having the 5' to 3' exonuclease activity and the first label, e.g., quencher molecule is released to induce signal change. The second label is remained on the solid substrate because of the resistance of the nucleotide labeled with the second label. Consequently, the signal change indicating the presence of the target nucleic acid sequence is obtained on the is solid substrate, thereby determining the presence of the target nucleic acid sequence.

In contrast, where the TD probe is hybridized with a non-target nucleic acid sequence, both the 5'-second hybridization portion and the separation portion form a single strand which is not digested by DNA polymerases having the 5' to 3' exonuclease activity. No cleavage fails to generate signal change.

According to a preferred embodiment, the second label is located on the 5'-second hybridization portion of the TD probe. The second label on the 5'-second hybridization portion is remained on the solid substrate because of the resistance of the nucleotide labeled with the second label, even when the TD probe is hybridized with the target nucleic acid sequence and then cleaved.

According to a preferred embodiment, the universal base in the separation portion is selected from the group consisting of deoxyinosine, inosine, 7-deaza-2'-daminosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-0-methoxyethyl inosine, 2'0-methoxyethyl nebularine, 2'-0-methoxyethyl 5-nitroindole, 2'-0-methoxyethyl 4-nitrobenzimidazole, 2'-0-methoxyethyl 3-nitropyrrole, and combinations thereof. More preferably, the universal base is deoxyinosine, 1-(2'-deoxy-beta-D-ribofuranosyl)-3-nitropyrrole or 5-nitroindole, most preferably, deoxyinosine.

Preferably, the separation portion comprises nucleotides having at least three, more preferably at least four, most preferably at least five universal bases. More is preferably, the separation portion comprises contiguous nucleotides having at least three, more preferably at least four, most preferably at least five universal bases. Alternatively, the separation portion comprises 3-10, 3-8, 4-7 or 4-5 contiguous universal bases.

Preferably, the 3'-first hybridization portion is longer than the 5'-second hybridization portion. The 3'-first hybridization portion is preferably 15-60 nucleotides, more preferably 15-40 nucleotides, still more preferably 15-30 nucleotides in length. Preferably, the 5'-second hybridization portion is at least 3, more preferably 5 and still more preferably 6 nucleotides in length. Preferably, the 5'-second hybridization portion is no more than 15, more preferably no more than 13 and still more preferably no more than 12 nucleotides in length. It is preferable that the 5'-second hybridization portion is 3-15 nucleotides, more preferably 3-13 nucleotides, still more preferably 4-12 nucleotides and most preferably 5-11 nucleotides in length. The separation portion is preferably 3-10 nucleotides, more preferably 3-8 nucleotides, still more preferably 4-7 nucleotides, most preferably 4-5 nucleotides in length. The length of both 5'-second hybridization portion and separation portion is preferably at least six, more preferably at least nine, still more preferably at least twelve and most preferably at least fifteen nucleotides.

According to a preferred embodiment, the $T_m$ of the 3'-first hybridization portion ranges from 40° C. to 80° C., more preferably 45° C. to 70° C. The $T_m$ of the 5'-second hybridization portion ranges preferably from 6° C. to 40° C. and more preferably from 10° C. to 40° C. The $T_m$ of the separation portion ranges preferably from 2° C. to 15° C. and more preferably 3° C. to 15° C.

According to a preferred embodiment, the second label is located on the 5'-second hybridization portion of the TD probe. More preferably, the second label on the 5'-second hybridization portion is located 2-15 nucleotides, still more preferably 2-10 nucleotides apart from the first label linked to the 5'-end of the 5'-second hybridization portion.

According to a preferred embodiment, the target nucleic acid sequence used in the present invention is a pre-amplified nucleic acid sequence by an amplification primer. The utilization of the pre-amplified nucleic acid sequence permits to increase the sensitivity and specificity of target detection of the present invention.

According to a preferred embodiment, the reverse primer or the amplification primer has a dual priming oligonucleotide (DPO) structure. The DPO structure possesses significantly higher target specificity than conventional primers as described in WO 2006/095981, of which teachings are incorporated into in its entity.

The term "conventional" in conjunction with primers or probes means any primer or probe not having the mDSO structure or the DPO structure. They are described herein as conventional primers or probes.

The present invention is well applicable to simultaneous (multiplex) detection of at least two target nucleic acid sequences. According to a preferred embodiment, the target nucleic acid sequence comprises at least two types (more preferably, at least three types, still more preferably at least five types) of nucleic acid sequences and the probe (and/or reverse primer) comprises at least two types (more preferably, at least three types, still more preferably at least five types) of probes.

Furthermore, the present invention is very useful in detection of a nucleotide variation. The term "nucleotide variation" used herein refers to a nucleotide polymorphism in a DNA sequence at a particular location among contiguous DNA segments that are otherwise similar in sequence. Such contiguous DNA segments include a gene or any other portion of a chromosome. For example, the nucleotide variation detected in the present invention includes SNP (single nucleotide polymorphism), deletion, insertion, substitution and translocation. Exemplified nucleotide variation includes numerous variations in a human genome (e.g., variations in the MTHFR (methylenetetrahydrofolate reductase) gene), variations involved in drug resistance of pathogens and tumorigenesis-causing variations. According to a preferred embodiment, the immobilized probe comprises a nucleotide corresponding to or complementary to a nucleotide variation.

In another aspect of this invention, there is provided a kit for detecting a target nucleic acid sequence from a DNA or a mixture of nucleic acids on a solid phase using a dual-labeled probe with resistance to a 5' to 3' exonuclease activity of a DNA polymerase, comprising:

(a) a solid substrate;
(b) an immobilized probe having a nucleotide sequence complementary to the target nucleic acid sequence; wherein the probe immobilized on a solid substrate through its 3'-end has an interactive dual label comprising a reporter molecule and a quencher molecule; the interactive dual label is positioned on the immobilized probe to induce energy quenching between the reporter molecule and the quencher molecule; a first label and a second label are selected from the reporter molecule and the quencher molecule; the first label is linked to the 5'-end of the immobilized probe and the second label is linked to a base of a nucleotide placed downstream of the first label, such that the linkage of the second label permits the nucleotide to have resistance to the 5' to 3' exonuclease activity of the DNA polymerase; and
(c) the DNA polymerase having the 5' to 3' exonuclease activity.

Since the kit of this invention is constructed to perform the detection method of the present invention described above, the common descriptions between them are omitted in order to avoid undue redundancy leading to the complexity of this specification.

According to a preferred embodiment, the first label is the quencher molecule and the second label is the reporter molecule. Alternatively, the first label is the reporter molecule and the second label is the quencher molecule.

According to a preferred embodiment, the second label is separated from the first label by a cleavage site on the immobilized probe by the 5' to 3' exonuclease activity. Preferably, the second label is located 2-20 nucleotides apart from the first label. More preferably, the second label is located 4-15 nucleotides apart from the first label.

According to a preferred embodiment, the first label is linked to a phosphate group of the 5'-end of the immobilized probe.

According to a preferred embodiment, the second label is linked to a thymine of a thymidine nucleotide in the immobilized probe.

Preferably, the DNA polymerase having the 5' to 3' exonuclease activity is a thermostable DNA polymerase having a 5' to 3' exonuclease activity.

According to a preferred embodiment, the kit further comprises a revere primer for producing copies of the target nucleic acid sequence to be hybridized with the immobilized probe.

According to a preferred embodiment, the immobilized probe is a target discriminative probe (TD probe) having a modified dual specificity oligonucleotide (mDSO) structure represented by the general formula I to allow for discrimination of a target nucleic acid sequence from a non-target nucleic acid sequence.

Preferably, the kit further comprises a primer set for amplifying the target nucleic acid sequence and the target nucleic acid sequence is a pre-amplified nucleic acid sequence.

According to a preferred embodiment, the target nucleic acid sequence comprises at least two types of nucleic acid sequences and the immobilized probe comprises at least two types of probes. Preferably, the target nucleic acid sequence comprises a nucleotide variation.

The present kits may optionally include the reagents required for performing target amplification PCR reactions (e.g., PCR reactions) such as buffers, DNA polymerase cofactors, and deoxyribonucleotide-5-triphosphates. Optionally, the kits may also include various polynucleotide molecules, reverse transcriptase, various buffers and reagents, and antibodies that inhibit DNA polymerase activity.

The kits may also include reagents necessary for performing positive and negative control reactions. Optimal amounts of reagents to be used in a given reaction can be readily determined by the skilled artisan having the benefit of the current disclosure. The kits, typically, are adopted to contain the constituents aforedescribed in separate packaging or compartments.

In still another aspect of this invention, there is provided a method for conferring resistance to a 5' to 3' exonuclease activity of a DNA polymerase to an oligonucleotide, comprising:

(a) determining a nucleotide sequence of the oligonucleotide; and (b) synthesizing the oligonucleotide with a label on a base of an nucleotide of the oligonucleotide whereby the nucleotide has resistance to the 5' to 3' exonuclease activity of the DNA polymerase.

Since the present invention relates to resistance of a base-labeled nucleotide to a 5' to 3' exonuclease activity of a DNA polymerase which is employed in the detection method above, the common descriptions between them are omitted in order to avoid undue redundancy leading to the complexity of this specification.

The nucleotide sequence of oligonucleotides may be determined to have a complementary sequence to a target nucleic acid sequence. The nucleotide sequence may have one or more mismatch nucleotides to a target nucleic acid sequence, so long as it may be specifically hybridized with the target nucleic acid sequence.

According to a preferred embodiment, the oligonucleotide is probe.

The synthesis of the oligonucleotide may be carried out by conventional methods such as the solid phase phosphoramidite triester method described by Beaucage and Caruthers, Tetrahedron Letts., 22(20):1859-1862 (1981), e.g., using an automated synthesizer, as described in Needham-VanDevanter et al. Nucleic Acids Res., 12:6159-6168 (1984).

According to a preferred embodiment, the nucleotide having the base linked with the label is an internal nucleotide of the oligonucleotide. The linkage of the label to the base component of the nucleotide may be carried out by conventional methods as described in Nelson, et al., Nucleic Acids Research 20(23):6253-6259 (1992); U.S. Pat. Nos. 4,757, 141, 5,559,767 and 5,231,191; and Haralambidis et al, Nucleic Acids Research, 15:4856-4876 (1987).

The base component linked with the label includes adenine, guanine, cytosine and thyamine, preferably thyamine.

It is preferable that the labeling of the base component by the label is made at a position not involved in hydrogen bonds with target nucleic acid sequences. For example, the label may be linked to the 5-carbon or 6-carbon of thyamine, preferably a methyl group of the 5-carbon of thyamine.

The features and advantages of the present invention will be summarized as follows:

(a) The present invention uses unique features in which the linkage of a label to a base component of a nucleotide of an oligonucleotide renders it to be resistant to the 5' to 3' exonuclease activity of DNA polymerase. Together with a dual-label system on probes immobilized on solid phase, such unique feature is applied to target detection system to suggest the present invention. When the immobilized probes having labels at its 5'-end and internal position is hybridized with the target nucleic acid sequence, it is progressively cleaved at its 5'-end in a 5' to 3-direction by the 5' to 3' exonuclease activity of DNA polymerases to release the label at its 5'-end. The cleavage reaction is terminated at the internal nucleotide labeled at its base component due to the resistance and the label to the internal nucleotide is finally remained in the solid substrate, finally providing signal change indicative of the presence of the target nucleic acid sequence.

(b) Because the second label is remained on the solid substrate by resistance to primer-independent 5' to 3' exonuclease activity of DNA polymerases due to labeling of a base component the internal nucleotide, the present invention requires no consideration of a suitability of position of the second label for remaining on the solid substrate. Unlikely, TaqMan probe-based methods on solid substrates using primer-dependent 5' to 3' nuclease activity of DNA polymerases, it is requisite that the position of the second label is strictly determined for remaining the second label on the solid substrate with considering reaction conditions.

(c) The present invention ensures to minimize background signal by positioning labels at a site on probes suitable to maximize quenching efficiency of the dual label system, since it permits to freely determine the position of the internal label on probes.

(d) The preferable probe used in this invention, the TD probe having the mDSO structure, contributes partly to removal of false positive signal that is generally generated by non-specific hybridization of conventional probes with non-target nucleic acid sequences.

(e) The present invention using the interactive dual label may measure signal change (signal decrease or increase) on a solid phase in an end-point or real-time manner, enabling quantitative analysis as well as qualitative analysis of target nucleic acid sequences.

(f) The present invention provides signal change by enzymatic reactions (by 5' to 3' exonuclease activity of DNA polymerases) as well as hybridization between probes and target nucleic acid sequences. In other words, a target specificity in the present invention is dually determined, successfully resolving problems of false positive results due to non-specific hybridization of probes. Furthermore, the cyclic repetition of the present invention enables immobilized probes to be involved in providing signal change and therefore to maximize the extent of the signal change.

(g) Unlike to TaqMan probe-based methods, the present invention may be performed only using immobilized probes with no use of primers. Therefore, the present invention is completely free from shortcomings associated with methods using multiple oligonucleotides such as difficulties in sequence selection of multiple oligonucleotides and optimization of reaction conditions and cost-ineffectiveness. Such advantage becomes more highlighted in multiplex target detection.

(h) Since the immobilized probes on the solid substrate are physically separated from one another, the present invention enables to simultaneously detect a multiple of target nucleic acid sequences on the solid substrate even when a single type of a dual label is used.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Evaluation of Resistance to 5' to 3' Exonuclease Activity of DNA Polymerase

We evaluated whether a nucleotide having a label linked to its base is resistant to 5' to 3' exonuclease activity of DNA polymerase.

For this evaluation, the synthetic oligonucleotide for *Staphylococcus aureus* (SA) gene was used as a template. Taq, Tth and Tfl DNA polymerases having a 5' nuclease activity was used for 5' to 3' exonucleolytic reaction. A dual-labeled probe was used in this evaluation. The probe has a fluorescent reporter molecule (FAM) linked to either the phosphate group at its 5'-end (SEQ ID NO: 2) or the thymine of a thymidine nucleotide (SEQ ID NOs: 3, 4, 5, 6 and 7) and has a quencher molecule (BHQ-1) at its 3'-end. The probes used in Examples were provided from Biosearch Technologies Inc. (USA). FAM containing a carbon spacer (C6 spacer) was used for preparing the probe (Biosearch Technologies Inc., USA).

The sequences of synthetic template and the probe used in this Example are:

```
                                                                        (SEQ ID NO: 1)
SAT         5'-GGTGTAGGTGGTGGCGGTAACAACGCCGTAAACCGAATGATTGACCACGGAATGAATAATGTT
GAATTTA-3'

(SEQ ID NO: 2)
SA-Con-M1        [FAM]TCAATCATTCGGTTTACGGCGTTG[BHQ-1]

(SEQ ID NO: 3)
SA-Con-D0(dT)    [T(FAM)]CAATCATTCGGTTTACGGCGTTG[BHQ-1]

(SEQ ID NO: 4)
SA-Con-D1(dT)    G[T(FAM)]CAATCATTCGGTTTACGGCGTTG[BHQ-1]

(SEQ ID NO: 5)
SA-Con-D3(dT)    TGG[T(FAM)]CAATCATTCGGTTTACGGCGTTG[BHQ-1]

(SEQ ID NO: 6)
SA-Con-D5(dT)    CGTGG[T(FAM)]CAATCATTCGGTTTACGGCGTTG[BHQ-1]

(SEQ ID NO: 7)
SA-Con-D8(dT)    TTCCGTGG[T(FAM)]CAATCATTCGGTTTACGGCGTTG[BHQ-1]

(Underlined letters indicate thymine linked with a fluorescent reporter molecule)
```

Cyclic exonucleolytic reaction was conducted in the final volume of 20 μl containing 0.5 pmole of synthetic template (SEQ ID NO: 1) for SA gene, 5 pmole of the probe (SEQ ID NO: 2, 3, 4, 5, 6 or 7), 2 μl of 10× reaction buffer (5 mM MgCl$_2$), 50 μM each of dNTPs, 2 units of Taq (Solgent, Korea), Tth (Epicentre Biotechnologies, US) or Tfl DNA polymerase (Epicentre Biotechnologies, US); the tube containing the reaction mixture was placed in the real-time thermocycler (CFX96, Bio-Rad); the reaction mixture was denatured for 2 min at 95° C. and subjected to 50 cycles of 20 sec at 95° C., 20 sec at 55° C. Detection of the signal was performed at 55° C. of each cycle.

As shown FIGS. 2, 3 and 4, the fluorescent signal was generated with the probe having a fluorescent reporter molecule linked to the phosphate group at its 5' end (SEQ ID NO: 2) in the presence of the target nucleic acid. No fluorescent signal was generated with the probes having a fluorescent reporter molecule linked to the thymine of a thymidine nucleotide (SEQ ID NOs: 3, 4, 5, 6 and 7) in the presence of the target nucleic acid. No fluorescent signals were generated in the absence of the target nucleic acid.

These results indicate that a nucleotide having a label at its base has resistance to a 5' to 3' exonuclease activity of DNA polymerase.

Example 2

Detection of Target Nucleic Acid Sequences Using Resistance to 5' To 3' Exonuclease Activity of DNA Polymerase with a Dual-labeled Probe on Microarray We applied the resistance of a nucleotide having a label linked to its base for the detection of target nucleic acid sequences on solid phase using a dual-labeled probe. Tao DNA polymerase having 5' nuclease activity was used for 5' to 3' exonucleolytic reaction.

The dual-labeled probe has a quencher molecule (BHQ-2) at its 5'-end and a fluorescent reporter molecule (Quasar570) linked to the thymine of an internal thymidine nucleotide. Quasar570 containing a carbon spacer (C6 spacer) was used for preparing the probe (Biosearch Technologies Inc., USA). BHQ-2 was linked through an additionally inserted carbon spacer (C6 spacer). The probe was immobilized on a glass slide by using an amino group (AminnoC7) at its 3'-end. A marker probe having a fluorescent reporter molecule (Quasar570) at its 5'-end was immobilized on the glass slide by using an amino group at its 3'-end. Synthetic oligonucleotide for *Staphylococcus aureus* (SA) was used as a template.

The sequences of synthetic template, dual-labeled probe and marker used in this Example are:

```
                                                                        (SEQ ID NO: 1)
SAT         5'-GGTGTAGGTGGTGGCGGTAACAACGCCGTAAACCGAATGATTGACCACGGAATGAATAATGTT
GAATTTA-3'

(SEQ ID NO: 8)
SA-Con-M    [BHQ-2][C6 spacer]TCATTCCG[T(Quasar570)]GGTCAATCATTCGGTTTACGGCGTTGTTACC
TTTTT[AminoC7]

(SEQ ID NO: 9)
Marker      [Quasar570]ATATATATAT[AminoC7]

(Underlined letters indicate thymine linked with a fluorescent reporter
molecule)
```

NSB9 NHS slides (NSBPOSTECH, Korea) were used for fabrication of the dual-labeled probe (SEQ ID NO: 8) and marker (SEQ ID NO: 9). The dual-labeled probe and marker dissolved in NSB spotting buffer at the final concentration of 50 μM were printed on the NSB9 NHS slides with PersonalArrayer™16 Microarray Spotter (CapitalBio, China). The dual-labeled probe and marker were spotted side by side in a 2×1 format (duplicate spots), and the resulting slide was incubated in a chamber maintained at ~85% humidity for overnight. The slides were then washed in a buffer solution containing 2×SSPE (0.3 M sodium chloride, 0.02 M sodium hydrogen phosphate and 2.0 mM EDTA), pH 7.4 and 7.0 mM SDS at 37° C. for 30 min to remove the non-specifically bound dual-labeled probe and marker and rinsed with distilled water. Then, the DNA-functionalized slides were dried using a slide centrifuge and stored in dark at 4° C. until use.

Exonulceolytic reaction was conducted in the final volume of 30 μl containing 10 pmole of synthetic template (SEQ ID NO: 1) for SA gene, 3 μl of 10× reaction buffer (6 mM MgCl$_2$), 200 μM each of dNTPs, 1.2 units of DiastarTaq DNA polymerase (Solgent, Korea); the whole mixture was applied to a chamber assembled on the surface of the slide on which the dual-labeled probe (SEQ ID NO: 8) was cross-linked. The slide was placed on in situ block in a thermocycler (GenePro B4I, China). The reaction was carried out as follows: 2 min denaturation at 95° C. and 60 min at 55° C. Finally, the slide was washed in distilled water for 1 min at 100° C. The image acquisition was carried out after each washing by the use of Confocal Laser Scanner, Axon GenePix4100A (Molecular Device, US) with scanning at 10-μm pixel resolution. The fluorescence intensity was analyzed by the use of quantitative microarray analysis software, GenePix pro6.0 software (Molecular Device, US). The fluorescence intensity was expressed as spot-medians after local background subtractions. Each spot was duplicated for the test of reproducibility. The fluorescence intensity indicates the average value of the duplicated spots.

As shown FIG. 5, the fluorescent signal (RFU: 65,486±0.7) was generated in the presence of the target nucleic acid. No fluorescent signal was generated in the absence of the target nucleic acid.

Example 3

Detection of Target Nucleic Acid Sequences Using Resistance to 5' To 3' Exonuclease Activity of DNA Polymerase with a Dual-labeled TD Probe on Microarray We applied the resistance of a nucleotide having a label linked to its base to 5' to 3' exonuclease activity of DNA polymerase for the detection of target nucleic acid sequences on solid phase using a dual-labeled TD probe. Taq DNA polymerase having 5' nuclease activity was used for 5' to 3' exonucleolytic reaction.

The dual-labeled TD probe has a quencher molecule (BHQ-2) at its 5'-end and a fluorescent reporter molecule (Quasar570) linked to the thymine of an internal thymidine nucleotide located on its 5'-second hybridization portion. Quasar570 containing a carbon spacer (C6 spacer) was used for preparing the probe (Biosearch Technologies Inc., USA). BHQ-2 was linked through an additionally inserted carbon spacer (C6 spacer). The TD probe was immobilized on a glass slide by using an amino group (AminnoC7) at its 3'-end. A marker probe having a fluorescent reporter molecule (Quasar570) at its 5'-end was immobilized on the glass slide by using an amino group at its 3'-end. Synthetic oligonucleotide for *Staphylococcus aureus* (SA) was used as a template.

The sequences of synthetic template, dual-labeled TD probe and marker used in this Example are:

```
                                                            (SEQ ID NO: 1)
SAT      5'-GGTGTAGGTGGTGGCGGTAACAACGCCGTAAACCGAATGATTGACCACGGAATGAATAATGTT

GAATTTA-3'

(SEQ ID NO: 10)
SA-TD-M  [BHQ2][C6 spacer]TCATTCCG[T(Quasar570)]GGIIIIII CATTCGGTTTACGGCGTTGTTACC TTTTT[AminoC7]

(SEQ ID NO: 9)
Marker   [Quasar570]ATATATATAT[AminoC7]

(Underlined letters indicate thymine linked with a fluorescent reporter molecule)
```

NSB9 NHS slides (NSBPOSTECH, Korea) were used for fabrication of the dual-labeled TD probe (SEQ ID NO: 10) and marker (SEQ ID NO: 9). The dual-labeled TD probe and marker dissolved in NSB spotting buffer at the final concentration of 50 μM were printed on the NSB9 NHS slides with PersonalArrayer'16 Microarray Spotter (CapitalBio, China). The dual-labeled TD probe and marker were spotted side by side in a 2×1 format (duplicate spots), and the resulting slide was incubated in a chamber maintained at ~85% humidity for overnight. The slides were then washed in a buffer solution containing 2×SSPE (0.3 M sodium chloride, 0.02 M sodium hydrogen phosphate and 2.0 mM EDTA), pH 7.4 and 7.0 mM SDS at 37° C. for 30 min to remove the non-specifically bound dual-labeled TD probe and marker and rinsed with distilled water. Then, the DNA-functionalized slides were dried using a slide centrifuge and stored in dark at 4° C. until use.

Exonucleolytic reaction was conducted in the final volume of 30 μl containing 10 pmole of synthetic template (SEQ ID NO: 1) for SA gene, 3 μl of 10× reaction buffer (6 mM MgCl$_2$), 200 μM each of dNTPs, 1.2 units of DiastarTaq DNA polymerase (Solgent, Korea); the whole mixture was applied to a chamber assembled on the surface of the slide on which the dual-labeled TD probe (SEQ ID NO: 10) was cross-linked. The slide was placed on in situ block in a thermocycler (GenePro B4I, China). The reaction was carried out as follows: 2 min denaturation at 95° C. and 60 min at 55° C. Finally, the slide was washed in distilled water for 1 min at 100° C. The image acquisition was carried out after each washing by the use of Confocal Laser Scanner, Axon GenePix4100A (Molecular Device, US) with scanning at 10-μm pixel resolution. The fluorescence intensity was analyzed by the use of quantitative microarray analysis software, GenePix pro6.0 software (Molecular Device, US). The fluorescence intensity was expressed as spot-medians after local background subtractions. Each spot was duplicated for the test of reproducibility. The fluorescence intensity indicates the average value of the duplicated spots.

As shown FIG. 6, the fluorescent signal (RFU: 65,486±0.0) was generated in the presence of the target nucleic acid. No fluorescent signal was generated in the absence of the target nucleic acid.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for detecting a target nucleic acid sequence from a DNA or a mixture of nucleic acids on a solid phase using a dual-labeled probe with resistance to an upstream oligonucleotide-independent 5' to 3' exonuclease activity of a DNA polymerase without the use of an upstream oligonucleotide, wherein the upstream oligonucleotide is an oligonucleotide positioned upstream of the 5'-end of an immobilized probe when the immobilized probe is hybridized with the target nucleic acid sequence, comprising:

(a) hybridizing the target nucleic acid sequence with the immobilized probe having a nucleotide sequence complementary to the target nucleic acid sequence; wherein the probe is immobilized on a solid substrate through its 3'-end and has an interactive dual label comprising a first label and a second label which are selected from a reporter molecule and a quencher molecule; the interactive dual label is positioned on the immobilized probe to induce energy quenching between the reporter molecule and the quencher molecule; the first label is linked to the 5'-end of the immobilized probe, such that the linkage of the first label does not render the 5'-end of the immobilized probe to be resistant to the upstream oligonucleotide-independent 5' to 3' exonuclease activity of the DNA polymerase and the second label is linked to a 5-carbon or 6-carbon of thymine base of a thymidine nucleotide placed downstream of the first label through a spacer having at least three carbon atoms; wherein the second label linked to the 5-carbon or 6-carbon of thymine base of the thymidine nucleotide renders the thymidine nucleotide to be resistant to the upstream oligonucleotide-independent 5' to 3' exonuclease activity of the DNA polymerase; wherein the thymidine nucleotide having the thymine base linked with the second label at its 5-carbon or 6-carbon through a spacer having at least three carbon atoms is an internal thymidine nucleotide of the immobilized probe; wherein the nucleotide sequence of the immobilized probe located downstream of the second label comprises a nucleotide sequence complementary to the target nucleic acid sequence;

(b) contacting the resultant of step (a) to the DNA polymerase having the upstream oligonucleotide-independent 5' to 3' exonuclease activity under conditions for cleavage of the immobilized probe without the use of an upstream oligonucleotide; wherein the immobilized probe hybridized with the target nucleic acid sequence is digested by the upstream oligonucleotide-independent 5' to 3' exonucleolytic reaction of the DNA polymerase to release the first label from the immobilized probe, resulting in change in a signal on the solid substrate;

(c) terminating the upstream oligonucleotide-independent 5' to 3' exonucleolytic reaction of the DNA polymerase at the internal thymidine nucleotide labeled with the second label; wherein the upstream oligonucleotide-independent 5' to 3' exonucleolytic reaction is terminated when the DNA polymerase encounters the internal thymidine nucleotide having the thymine base linked with the second label at its 5-carbon or 6-carbon through a spacer having at least three carbon atoms; wherein the second label linked to the 5-carbon or 6-carbon of thymine base of the internal thymidine nucleotide renders the internalthymidine nucleotide to be resistant to the upstream oligonucleotide-independent 5' to 3' exonuclease activity of the DNA polymerase; wherein the second label is remained on the solid substrate; and (d) detecting the signal change on the solid substrate, such that the signal change by the cleavage of the immobilized probe is indicative of the presence of the target nucleic acid sequence.

2. The method according to claim 1, wherein the second label is separated from the first label by a cleavage site on the immobilized probe by the upstream oligonucleotide-independent 5' to 3' exonuclease activity.

3. The method according to claim 1, wherein the second label is located 2-20 nucleotides apart from the first label.

4. The method according to claim 1, wherein the first label is linked to a phosphate group of the 5'-end of the immobilized probe.

5. The method according to claim 1, wherein the method further comprises repeating steps (a)-(b) or (a)-(c) with denaturation between repeating cycles.

6. The method according to claim 1, wherein the detection of the step (d) is performed in a real-time manner, an end-point manner or a predetermined time interval manner.

7. The method according to claim 1, wherein the DNA polymerase having the upstream oligonucleotide-independent 5' to 3' exonuclease activity is a thermostable DNA polymerase having a upstream oligonucleotide-independent 5' to 3' exonuclease activity.

8. The method according to claim 1, wherein the step (a) further comprises a reverse primer for producing copies of the target nucleic acid sequence to be hybridized with the immobilized probe wherein the reverse primer is positioned downstream of the 3'-end of the immobilized probe and hybridized with an opposite strand of the target nucleic acid sequence.

9. The method according to claim 1, wherein the target nucleic acid sequence comprises at least two types of nucleic acid sequences and the immobilized probe comprises at least two types of probes.

10. The method according to claim 1, wherein the target nucleic acid sequence comprises a nucleotide variation.

11. A kit for detecting a target nucleic acid sequence from a DNA or a mixture of nucleic acids on a solid phase using a dual-labeled probe with resistance to an upstream oligonucleotide-independent 5' to 3' exonuclease activity of a DNA polymerase without the use of an upstream oligonucleotide wherein the upstream oligonucleotide is an oligonucleotide positioned upstream of the 5'-end of an immobilized probe when the immobilized probe is hybridized with the target nucleic acid sequence, comprising:

(a) a solid substrate;

(b) the immobilized probe having a nucleotide sequence complementary to the target nucleic acid sequence; wherein the probe is immobilized on a solid substrate through its 3'-end and has an interactive dual label comprising a first label and a second label which are selected from a reporter molecule and a quencher molecule; the interactive dual label is positioned on the immobilized probe to induce energy quenching between the reporter molecule and the quencher molecule; the first label is linked to the 5'-end of the immobilized probe, such that the linkage of the first label does not render the 5'-end of the immobilized probe to be resistant to the upstream oligonucleotide-independent 5' to 3' exonuclease activity of the DNA polymerase and the second label is linked to a 5-carbon or 6-carbon of thymine base of a thymidine nucleotide placed downstream of the first label through a spacer having at least three carbon atoms; wherein the second label linked to the 5-carbon or 6-carbon of thymine base of the thymidine nucleotide renders the thymidine nucleotide to be resistant to the upstream oligonucleotide-independent 5' to 3' exonuclease activity of the DNA polymerase; wherein the thymidine nucleotide having the thymine base linked with the second label at its 5-carbon or 6-carbon through a spacer having at least three carbon atoms is an internal thymidine nucleotide of the immobilized probe; wherein the nucleotide sequence of the immobilized probe located downstream of the second label comprises a nucleotide sequence complementary to the target nucleic acid sequence; and (c) the DNA polymerase having the upstream oligonucleotide-independent 5' to 3' exonuclease activity.

12. The kit according to claim 11, wherein the second label is separated from the first label by a cleavage site on the immobilized probe by the upstream oligonucleotide-independent 5' to 3' exonuclease activity.

13. The kit according to claim 11, wherein the second label is located 2-20 nucleotides apart from the first label.

14. The kit according to claim 11, wherein the first label is linked to a phosphate group of the 5'-end of the immobilized probe.

15. The kit according to claim 11, wherein the DNA polymerase having the upstream oligonucleotide-independent 5' to 3' exonuclease activity is a thermostable DNA polymerase having an upstream oligonucleotide-independent 5' to 3' exonuclease activity.

16. The kit according to claim 11, wherein the kit further comprises a reverse primer for producing copies of the target nucleic acid sequence to be hybridized with the immobilized probe wherein the reverse primer is positioned downstream of the 3'-end of the immobilized probe and hybridized with an opposite strand of the target nucleic acid sequence.

17. The kit according to claim 11, wherein the target nucleic acid sequence comprises at least two types of nucleic acid sequences and the immobilized probe comprises at least two types of probes.

18. The kit according to claim 11, wherein the target nucleic acid sequence comprises a nucleotide variation.

* * * * *

SEQUENCE LISTING

<160> NUMBER OF SEQ ID NOS: 10

<210> SEQ ID NO 1
<211> LENGTH: 70
<212> TYPE: DNA
<213> ORGANISM: Artificial Sequence
<220> FEATURE:
<223> OTHER INFORMATION: Synthetic Construct

<400> SEQUENCE: 1
ggtgtaggtg gtggcggtaa caacgccgta aaccgaatga ttgaccacgg aatgaataat     60
gttgaattta                                                           70

<210> SEQ ID NO 2
<211> LENGTH: 24
<212> TYPE: DNA
<213> ORGANISM: Artificial Sequence
<220> FEATURE:
<223> OTHER INFORMATION: Synthetic Construct

<400> SEQUENCE: 2
tcaatcattc ggtttacggc gttg                                           24

<210> SEQ ID NO 3
<211> LENGTH: 24
<212> TYPE: DNA
<213> ORGANISM: Artificial Sequence
<220> FEATURE:
<223> OTHER INFORMATION: Synthetic Construct

<400> SEQUENCE: 3
tcaatcattc ggtttacggc gttg                                           24

<210> SEQ ID NO 4
<211> LENGTH: 25
<212> TYPE: DNA
<213> ORGANISM: Artificial Sequence
<220> FEATURE:
<223> OTHER INFORMATION: Synthetic Construct

<400> SEQUENCE: 4
gtcaatcatt cggtttacgg cgttg                                          25

<210> SEQ ID NO 5
<211> LENGTH: 27
<212> TYPE: DNA
<213> ORGANISM: Artificial Sequence
<220> FEATURE:
<223> OTHER INFORMATION: Synthetic Construct

<400> SEQUENCE: 5
tggtcaatca ttcggtttac ggcgttg                                        27

<210> SEQ ID NO 6
<211> LENGTH: 29
<212> TYPE: DNA
<213> ORGANISM: Artificial Sequence
<220> FEATURE:
<223> OTHER INFORMATION: Synthetic Construct

```
<400> SEQUENCE: 6
cgtggtcaat cattcggttt acggcgttg                                        29

<210> SEQ ID NO 7
<211> LENGTH: 32
<212> TYPE: DNA
<213> ORGANISM: Artificial Sequence
<220> FEATURE:
<223> OTHER INFORMATION: Synthetic Construct

<400> SEQUENCE: 7
ttccgtggtc aatcattcgg tttacggcgt tg                                    32

<210> SEQ ID NO 8
<211> LENGTH: 45
<212> TYPE: DNA
<213> ORGANISM: Artificial Sequence
<220> FEATURE:
<223> OTHER INFORMATION: Synthetic Construct

<400> SEQUENCE: 8
tcattccgtg gtcaatcatt cggtttacgg cgttgttacc ttttt                      45

<210> SEQ ID NO 9
<211> LENGTH: 10
<212> TYPE: DNA
<213> ORGANISM: Artificial Sequence
<220> FEATURE:
<223> OTHER INFORMATION: Synthetic Construct

<400> SEQUENCE: 9
atatatatat                                                             10

<210> SEQ ID NO 10
<211> LENGTH: 45
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (12)..(16)
<223> OTHER INFORMATION: n denotes deoxyinosine

<400> SEQUENCE: 10
tcattccgtg gnnnnncatt cggtttacgg cgttgttacc ttttt                      45
```